(12) United States Patent
Majeed et al.

(10) Patent No.: US 9,579,352 B2
(45) Date of Patent: Feb. 28, 2017

(54) **PROCESS FOR THE THERAPEUTIC MANAGEMENT OF DIARRHEA PREDOMINANT IRRITABLE BOWEL SYNDROME USING *BACILLUS COAGULANS* SBC-37-01, MTCC 5856**

(71) Applicants: Muhammed Majeed, Edison, NJ (US); Kalyanam Nagabhushanam, East Windsor, NJ (US); Natarajan Sankaran, Bangalore (IN); Priti Vaidyanathan, Bangalore (IN); Sivakumar Arumugam, Bangalore (IN); Suresh Kumar Karri, Bangalore (IN)

(72) Inventors: Muhammed Majeed, Edison, NJ (US); Kalyanam Nagabhushanam, East Windsor, NJ (US); Natarajan Sankaran, Bangalore (IN); Priti Vaidyanathan, Bangalore (IN); Sivakumar Arumugam, Bangalore (IN); Suresh Kumar Karri, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 14/536,701

(22) Filed: Nov. 10, 2014

(65) Prior Publication Data

US 2016/0129054 A1  May 12, 2016

(51) Int. Cl.
*A01N 63/00* (2006.01)
*A61K 35/742* (2015.01)
*A61K 35/00* (2006.01)

(52) U.S. Cl.
CPC ...... *A61K 35/742* (2013.01); *A61K 2035/115* (2013.01)

(58) Field of Classification Search
None
See application file for complete search history.

(56) References Cited

U.S. PATENT DOCUMENTS 7,767,203 B2 * 8/2010 Farmer .................... A23L 1/30
424/93.46

OTHER PUBLICATIONS

Gluten-Free Remedies "Restore gut Health with probiotics", Dec. 2011, 4 pages of PDF.*

* cited by examiner

*Primary Examiner* — Kade Ariani

(57) ABSTRACT

The present invention discloses a process for the therapeutic management of diarrhea predominant irritable bowel syndrome in humans comprising the oral administration of *Bacillus coagulans* SBC37-01, MTCC 5856 (containing not less than 2 billion spores) along with standard treatment of care in a specific manner.

3 Claims, 7 Drawing Sheets

A value of '0' indicates no pain while '10' indicates 'worst possible pain'

*p<0.01 reached statistical significance between placebo and *Bacillus Coagulans* SBC37-01, MTCC 5856 groups on visit 3 & 4.

*p<0.01 between placebo and *Bacillus Coagulans* SBC37-01, MTCC 5856 groups on visits 2 to 4

*p<0.01 between placebo and *Bacillus Coagulans* SBC37-01, MTCC 5856 groups on visits 2 to 4

*p<0.01 between placebo and *Bacillus coagulans* SBC37-01, MTCC 5856 groups on visits 3 & 4

*p<0.01 between placebo and *Bacillus coagulans* SBC37-01, MTCC 5856 groups on visits 3 & 4

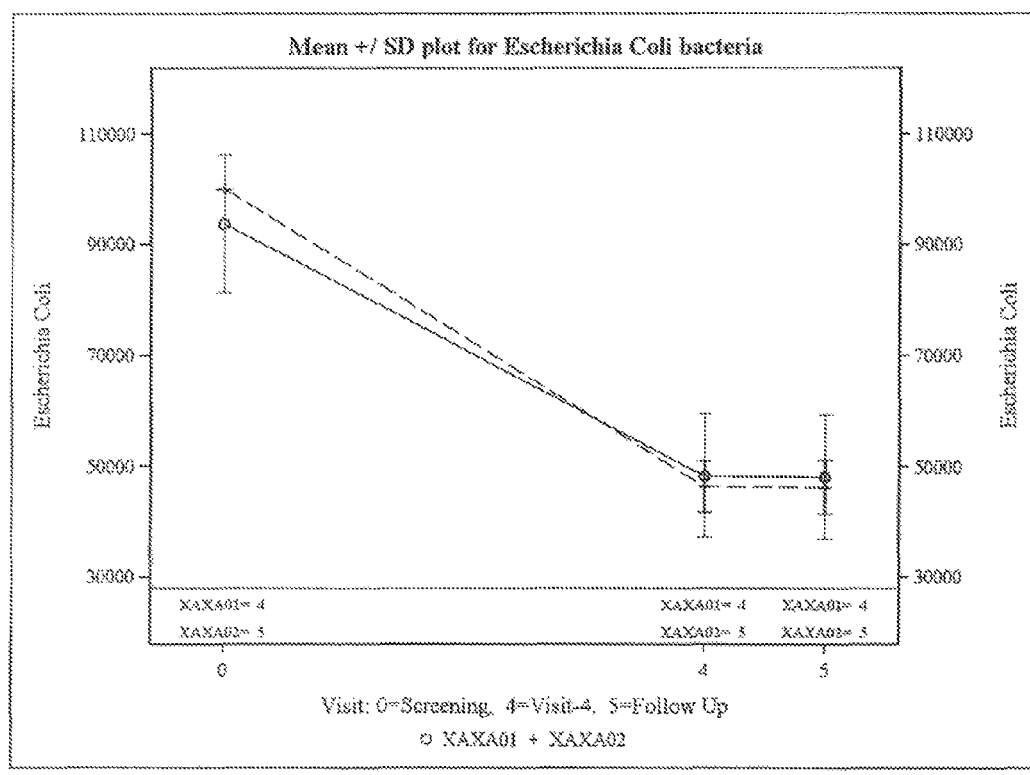

PROCESS FOR THE THERAPEUTIC MANAGEMENT OF DIARRHEA PREDOMINANT IRRITABLE BOWEL SYNDROME USING *BACILLUS COAGULANS* SBC-37-01, MTCC 5856

BACKGROUND OF THE INVENTION

Field of the Invention

The present invention in general relates to probiotic formulations and their therapeutic effects. In specific, the present invention discloses a process for the therapeutic management of diarrhea predominant irritable bowel syndrome in humans comprising the oral administration of *Bacillus Coagulans* SBC37-01, MTCC 5856 (containing not less than 2 billion spores) along with standard treatment of care in a specific manner.

Description of Prior Art

The World Health Organization's 2001 definition of probiotics is "live microorganisms which, when administered in adequate amounts, confer a health benefit on the host" and are able to prevent or improve some diseases (Eric P (2007) Probiotics and prebiotics renaissance of a therapeutic principle. Cent Eur J Med 2: 237-270). Consumption of probiotics is associated with a range of health benefits including stimulation of the immune system, protection against diarrheal diseases and nosocomial and respiratory tract infections, lowering of cholesterol, attenuation of overt immunoinflammatory disorders and anticancer effects (Britton R, Versalovic J (2008) Probiotics and Gastrointestinal Infections. Interdisciplinary Perspectives on Infect Dis 2008: 1-10, and Gill H, Prasad J (2008) Bioactive Components of milk: Probiotics, immunomodulation, and health benefits, in Advances in Experimental Medicine and Biology, ed by Bösze Z. Springer, New York USA, pp 423-454). Most probiotic microorganisms belong to the genera *Lactobacillus* and *Bifidobacterium*; however, other bacteria and some yeast may also have probiotic properties. Lactobacilli are usually described as Gram-positive, non-spore-forming and non-flagelated rods or cocobacilli, aerotolerant, fastidious, acid-tolerant, and strictly fermentative. The commercial interest in functional foods containing probiotics matches with the increasing study of their role in the digestive tract (Figueroa-González I, Quijano G, Ramirez G, Cruz-Guerrero A (2011) Probiotics and Prebiotics—perspectives and challenges. J Sci Food Agric 91: 1341-1348). Some probiotics have been shown in preliminary research to possibly treat various forms of gastroenteritis (Longstreth G F, Thompson W G, Chey W D, Houghton L A, Mearin F, Spiller R C: Functional bowel disorders. Gastroenterology 2006, 130(5):1480-1491). Irritable bowel syndrome (IBS), a common functional gastrointestinal (GI) disorder, is characterized by abdominal pain or discomfort, diarrhoea, constipation, abdominal bloating and flatulence, which are associated with changes in the frequency and form of stool and may markedly lower the quality of life (King C K, Glass R, Bresee J S, Duggan C (November 2003). Managing acute gastroenteritis among children: oral rehydration, maintenance, and nutritional therapy. *MMWR Recomm Rep* 52 (RR-16): 1-16, Vasiljevic T, Shah N P (2008) Probiotics—From Metchnikoff to bioactives. Int Dairy J 18: 714-728 and Tuohy K M, Probert H M, Smejkal C W, Gibson G R (2003) Using probiotics and prebiotics to improve gut health. Drug Discov Today 8: 692-699). Probiotic administration, prevent the invasion of tight junctions or modulation of gut microbiota composition and/or activity might bring about relief in IBD symptoms or maintain remission from clinical symptoms (Santosa S, Farnworth E, Jones P (2006) Probiotics and Their Potential Health Claims. Nutr Rev 64: 265-274). It is important to note that health benefits provided by probiotics are strain specific, and not species- or genus-specific. Therefore, no probiotic strain will provide all proposed benefits, not even strains of the same species, and not all strains of the same species will be effective against defined healthy conditions Figueroa-González I, Quijano G, Ramírez G, Cruz-Guerrero A (2011) Probiotics and Prebiotics—perspectives and challenges. J Sci Food Agric 91: 1341-1348.

It is the principle objective of the present invention to disclose a process for the therapeutic management of diarrhea predominant irritable bowel syndrome in humans comprising the oral administration of *Bacillus Coagulans* SBC37-01, MTCC 5856 along with standard treatment of care. The present invention fulfills stated objective and provided further related advantages of enhancing therapeutic efficacy for irritable bowel syndrome by using/incorporating *Bacillus coagulans* SBC37-01 in the standard therapeutic regimen in a specific manner. *Bacillus coagulans* SBC37-01 is a proprietary strain of Sami Labs Limited, Bangalore, India and Sabinsa Corporation, NJ, USA that has been deposited in the Microbial Type Culture Collection and Gene Bank (MTCC), a national facility established and funded jointly by the Department of Biotechnology (DBT) and the Council of Scientific and Industrial Research (CSIR), Government of India. *Bacillus coagulans* SBC37-01 has been assigned the strain number MTCC 5856 and exhibits 99% genetic homology with the known bacterial strains *Bacillus coagulans* ATCC 31284, *Bacillus coagulans* NBRC 3887 and *Bacillus coagulans* ATCC 7050.

Deposit of Biological Material

The deposit of biological material *Bacillus coagulans* SBC37-01 bearing accession number MTCC 5856, mentioned in the instant application has been made on $19^{th}$ Sep. 2013 at Microbial Type Culture Collection & Gene Bank (MTCC), CSIR-Institute of Microbial Technology, Sector 39-A, Chandigarh—160036, India.

SUMMARY OF THE INVENTION

Disclosed is a process for the therapeutic management of diarrhea predominant irritable bowel syndrome in humans comprising the oral administration of *Bacillus Coagulans* SBC37-01, MTCC 5856 along with standard treatment of care. Illustrative examples wherein the standard treatment regimen comprises Sompraz D (containing Domperidone 30 mg and 40 mg of Esomeprazole) and Metrogyl 400 (Metronidazole 400 mg) once a day have been included in the instant specification. The present invention provides the advantage of enhancing therapeutic efficacy for irritable bowel syndrome by using/incorporating *Bacillus coagulans* SBC37-01, MTCC 5856 in the standard therapeutic regimen in a specific manner.

Other features and advantages of the present invention will become apparent from the following more detailed description, taken in conjunction with the accompanying images, which illustrate, by way of example, the principle of the invention.

DESCRIPTION OF THE FIGURES

FIG. 7 shows the Mean+/SD plot for *Escherichia coli* bacteria in stools.

DESCRIPTION OF THE MOST PREFERRED EMBODIMENT

Figure 1:
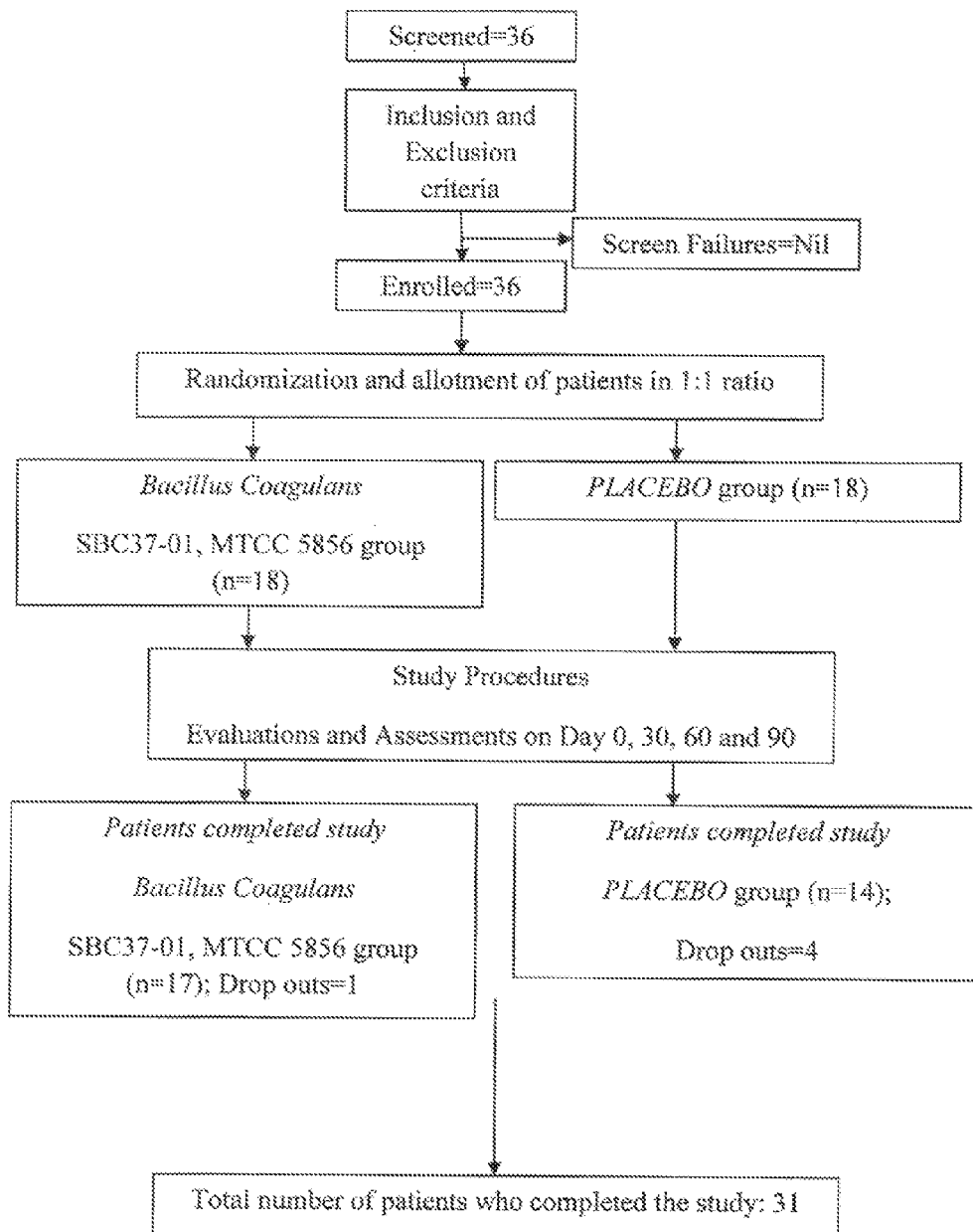
FIG. 1 shows the flow chart for the study procedures.

In the most preferred embodiment, the present invention relates to a process for the therapeutic management of diarrhea predominant irritable bowel syndrome in humans newly diagnosed with mild to moderate irritable bowel syndrome or previously untreated patients with mild to moderate irritable bowel syndrome, said process comprising step of orally administering *Bacillus Coagulans* SBC37-01, MTCC 5856 formulation containing not less than 2 billion spores at least 30 minutes before a meal, preferably as a dietary supplement in the morning for a period of 90 days along with standard treatment of care once a day in a manner that a time gap of 4 hours is maintained between the administration of said dietary supplement and the standard treatment of care and said process results in enhancing the assessed therapeutic efficacy of the standard treatment of care through amelioration of symptoms associated with irritable bowel syndrome (IBS). Sompraz D (containing Domperidone 30 mg and 40 mg of Esomeprazole) and Metrogyl 400 (Metronidazole 400 mg) as a standard therapeutic regimen for irritable bowel syndrome has been included and discussed in the illustrative example set forth herein below.

The following example is incorporated herein below as illustrative examples of the most preferred embodiment of the instant invention.

Example 1

Objective & Rationale of the Clinical Study

To evaluate formulations containing *Bacillus coagulans* SBC37-01, MTCC 5856 as dietary supplement in patients receiving standard care of treatment for diarrhea predominant Irritable Bowel Syndrome.

Ethics:

This research was conducted in accordance with the clinical research guidelines established by the Drugs and Cosmetics Act, 1940 of India, Drugs and Cosmetics Rules, 1945 of India, Ethical Guidelines for Biomedical Research on Human Participants, 2006 of Indian Council of Medical Research (ICMR) in India, the principles enunciated in the Declaration of Helsinki (Edinburgh, 2000) and the ICH-harmonized tripartite guideline regarding Good Clinical Practice (GCP).

Subject Information and Consent:

Written and oral information about the study in a language understandable by the subject was provided to all subjects. Each subject was informed by the investigator, prior to the screening evaluation, of the purpose of this clinical trial, including possible risks and benefits and documented the informed consent process in the subject's chart. Sufficient time was provided for each subject to decide whether to participate in the study and all the questions and clarifications regarding the study were clarified by the investigator.

Selection of Study Subjects:

In this multi-centered study, subjects were included in the study if indicated "Yes" to all of the inclusion criteria and "No" to all of the exclusion criteria.

Inclusion Criteria

1. Male or female subjects ranging in age from 18 to 55 years (both inclusive) diagnosed as having gastro intestinal disorders and based on the medical history record were included in the study by the Investigator.
2. Fulfilling Rome III Diagnostic Criteria for Functional IBS (Functional Diarrhea). Criterion fulfilled for the last 3 months with symptom onset at least 6 months prior to diagnosis a) Recurrent abdominal pain or discomfort (uncomfortable sensation not described as pain) at least 3 days/month in the last 3 months associated with two or more of the following:
i. Improvement with defecation
ii. Onset associated with a change in frequency of stool
iii. Onset associated with a change in form (appearance) of stool
b) Recurrent feeling of bloating or visible distension at least 3 days/month in the last 3 months
c) Loose (mushy) or watery stools without pain occurring in at least 75% of stools 3. Willingness to follow the protocol requirement as evidenced by written, informed consent.
4. Willingness to complete subject diaries and respond to study questionnaires.
5. Agree not to use any other medication (prescription and over the counter), including vitamins and minerals, during the course of this study.
6. Agree not to use any yogurt during the course of this study.
7. Subjects whose blood chemistries are within a normal range or not considered clinically significant if outside the normal range
8. Subject's assurance that they have not taken antibiotics or other products whose primary site of action is in the GIT for a period up to 1 month prior to the start of the study.

Exclusion Criteria
1. Sufficient criteria for a diagnosis of functional dyspepsia or other functional GI disorder.
2. Any clinically significant medical history, medical finding or an ongoing medical or psychiatric condition exists which in the opinion of the Investigator could jeopardize the safety of the subject, impact validity of the study results or interfere with the completion of study according to the protocol.
3. Significant abnormal findings as determined by baseline history, physical examination, vital signs (blood pressure, pulse rate, respiration rate) hematology, serum chemistry, urinalysis.
4. History or presence of significant alcoholism or product abuse in the past one year.
5. Participation in a clinical study during the preceding 90 days.
6. History of malignancy or other serious disease.
7. Any contraindication to blood sampling.
8. Smoking or Consumption of tobacco products.
9. Blood or blood products donated in past 30 days prior to study supplement administration.
10. Female subjects on pregnancy and lactating women.

Safety and Efficacy Outcomes:

The safety outcomes were measured by: 1] Physical Examination & Vitals, 2] Assessment of Reported Adverse events, if any, 3] Assessment for any abnormal laboratory parameters as compared to Baseline. The primary efficacy outcomes were measured by 1] Self assessment of abdominal pain, measured on a 10 cm Visual Analog Scale-VAS, 2] Bloating as measured by Gastro intestinal discomfort questionnaire 3] Difference in average stool frequency during weeks 11-12 of the treatment period and consistency by subjective evaluation using Bristol Stool Form Score. The secondary efficacy outcomes were measured by 1] Physician's Global Assessment, 2] Irritable Bowel Syndrome Quality of Life 3] Pathogenic bacteria count in stools. Subjects recorded stool frequency and form, urgency, bloating, abdominal pain and a global satisfaction with control of IBS scored each week.

Study Design & Methodology:

This was a randomized, double blind, parallel group, placebo controlled study to evaluate the safety and efficacy of *Bacillus coagulans* SBC37-01, MTCC 5856 in patients with diarrhea predominant Irritable Bowel Syndrome administered as tablets, for 90 days in enrolled subjects. Screening: Signed Informed Consent form was obtained; demographic data, medical history, medication history, physical examination, vital signs, blood sample for laboratory analysis, urine sample for urine pregnancy test was performed/examined and recorded during this visit. Subjects were provided with sterile containers and were advised on collection of their respective stool sample tests (to eliminate amoebiasis patients and to quantify pathogenic bacteria). Day 0: Evaluation for Inclusion & Exclusion Criteria, eligible subjects were enrolled into the study during this visit. Subjects were instructed on their daily dose of study supplement. Subjects were provided with study visit plan, patient diary. Physical examination, Vital signs were documented in the respective CRFs. Visual Analog Scale for abdominal pain-VAS, Gastrointestinal discomfort questionnaire, Bristol stool form score, irritable bowel syndrome quality of life questionnaire were filled during this visit which served as baseline values. Physician's global assessments were conducted. In this visit Subjects were randomized to receive either or Placebo. Day 30 & Day 60: Study supplements were provided to all subjects as per the randomization code, subjects were instructed to take their daily *Bacillus coagulans* SBC37-01, MTCC 5856 tablets or Placebo on days not coming to the clinic along with their standard of care treatment. Subjects were provided with study supplements (tablets) as per their randomization code, to last until the next visit. Subjects recorded their daily food intake details in the subject diary. VAS, Gastrointestinal discomfort questionnaire, Bristol stool form score, Irritable bowel syndrome quality of life questionnaire was evaluated and documented. Physician's global assessment was conducted. Reports on Adverse Events by the subjects were captured on their respective Case Report Forms by the site personnel. Concomitant medications, if any, were recorded. Day 90: Physical examination & Vital signs were recorded. VAS, Gastrointestinal discomfort questionnaire, Bristol stool form score, Irritable bowel syndrome quality of life questionnaire was evaluated and documented. Physician's global assessment was conducted. Blood sampling for serum chemistry & hematology was performed and compared with base line values. Stool sample culture for quantification of pathogenic bacteria was performed. Subjects submitted their subject diaries and returned the unused study supplements. Reports on Adverse Events by the subjects were captured on their respective Case Report Forms. Concomitant medications, if any, were recorded. Day 105 (Follow up Visit): Patients were inquired on incidence of Adverse Events, if any, since his/her last visit. Stool sample culture for quantification of pathogenic bacteria was performed. The schedule of events is depicted in Table 3.

Study Procedures:

The assigned *Bacillus coagulans* SBC37-01, MTCC 5856 study product was double blinded, i.e., neither the subjects nor the study staff knew the treatment group assigned until study completion. Eligible subjects were randomized in a 1:1 ratio (*Bacillus coagulans* SBC37-01, MTCC 5856: Placebo) in a randomly-permuted order by computer at the sponsor center. Each participant was assigned a 6-digit randomization code between and the respective site personnel dispensed the study supplements as per the randomization code list shared with them by the sponsor. Clinical site staff and participants remained blinded to the treatment received throughout the course of the study. Double blinding was accomplished by independent blinding of the dosing kits. Newly diagnosed or untreated patients who were not on any other treatment in the past 3 months with mild to moderate IBS in severity were enrolled into the study. Sompraz D (containing Domperidone 30 mg and 40 mg of Esomeprazole) & Metrogyl 400 (Metronidazole 400 mg) once a day was considered as standard treatment of care for diarrhea predominant IBS, by the three clinical sites' investigators for all the study subjects. Additionally, subjects were asked to self administer one Tablet per day (either *Bacillus coagulans* MTCC 5856 or Placebo) at least 30 minutes before a meal, preferably in the morning as a dietary supplement for a period of 90 days. This is subject to, a gap between the dietary supplement and standard drugs of treatment for diarrhea predominant IBS is at least 4 hours. Subjects used this product on an outpatient basis and were scheduled to return for clinical evaluation at Day 30, Day 60 and Day 90 and Day 105. The dosing period was for 90 days. Compliance with study medication was reviewed at each visit. This was by examination of the returned medication. All accountability records were incorporated into the investigator's study file. The patients were instructed against the use of any kind of yoghurt during the study duration. The daily food intake of the patients was recorded in the patient diaries provided to them at Visit 1. The same was checked and verified at subsequent visits by the investigators. No interim analysis was done during the study period. The respective hospital laboratories were used for all assessments pertaining to this study. Clinical trial monitors who were independent of the study staff monitored the progress of all clinical investigations that were conducted and ensured that the protocol is adhered in all aspects. Data collection during this clinical study and statistical analysis were performed by separate functional groups and independent statistician respectively.

Statistical Analysis:

As this is a pilot study, no formal sample size calculation was performed. The baseline values of VAS, Gastro-Intestinal disturbances questionnaire, Bristol Stool Form Score, Physician's Global Assessment and IBS Quality of Life questionnaire were compared to that of end of study visit by appropriate statistical tools. Statistical Analysis Software (SAS) of version 9.2 software was used for data analysis here. Paired 't' test, Analysis of Covariance (ANCOVA) and Wilcoxon signed rank sum test were used for appropriate data set variables to reach the best possible statistical conclusion between the *Bacillus coagulans* SBC37-01, MTCC 5856 receiving and Placebo receiving groups. The baseline descriptors were summarized as means and standard deviations for continuous variables and as frequencies and percentages for categorical variables. Last Observation Carry Forward (LOCF) method was followed for efficacy evaluations of subjects, whose data was not available in the last/final visit.

Results:

At screening, the median age of all the enrolled subjects was 35.5 years whereas it was 35.8±10.91 (mean±SD), median height was 163.0 cms (163.8±7.67), median weight was 63.0 Kg (65.3±10.11). The median BMI being 24.1 Kg/m$^2$ (24.4±3.06) with 17 males (47.22%) and 19 females (52.78%) enrolled into the study. While 34 (94.44%) were non users of tobacco or tobacco products, 35 (97.22%) were non drinkers. There were no statistically significant changes in the body weight and BMI from baseline to visit 4 (Table 2) or between the treatment groups. All the safety and efficacy assessments were done at various study visits, as per schedule of events (Table 3) and as amoebiasis and diarrhea predominant IBS share few clinical symptoms in common, Table 4 shows that the patients enrolled into the study were not suffering from amoebiasis (as a part of exclusion criteria), thereby enrolling IBS patients exclusively into this study.

(A) SAFETY: No clinically significant abnormal lab values were identified and no statistically significant changes in the vitals (table 6) were observed from the baseline to final visits. There was a single Adverse Event reported during the entire study period and as per the Investigator's opinion, the event was 'unrelated' to the study product. There were no Serious Adverse Events or Significant Adverse Events noticed in this study.

Figure 2:
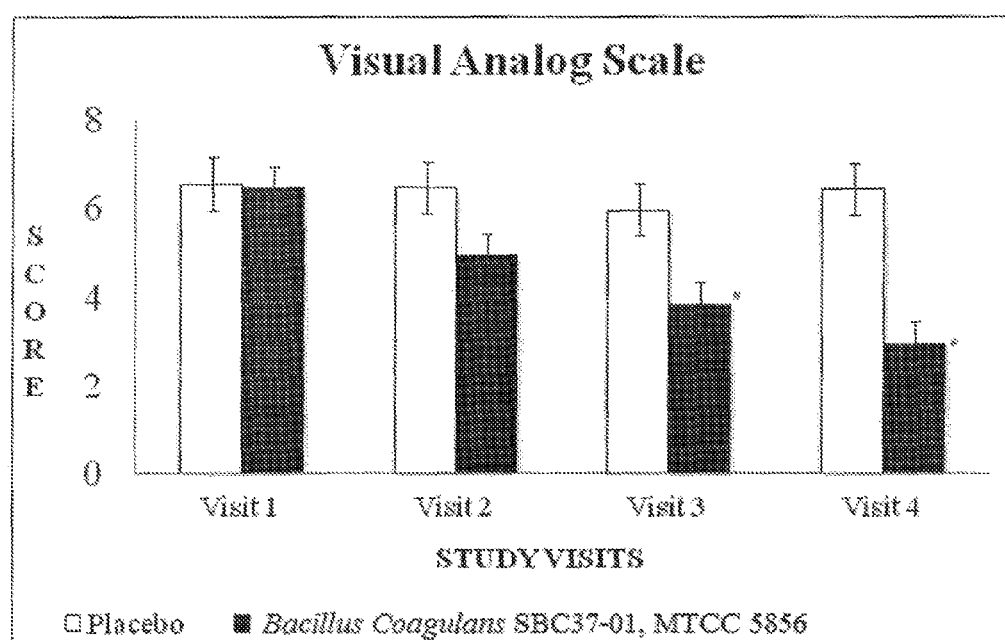
FIG. 2 shows the visual analog scale for abdominal pain.
Figure 3:
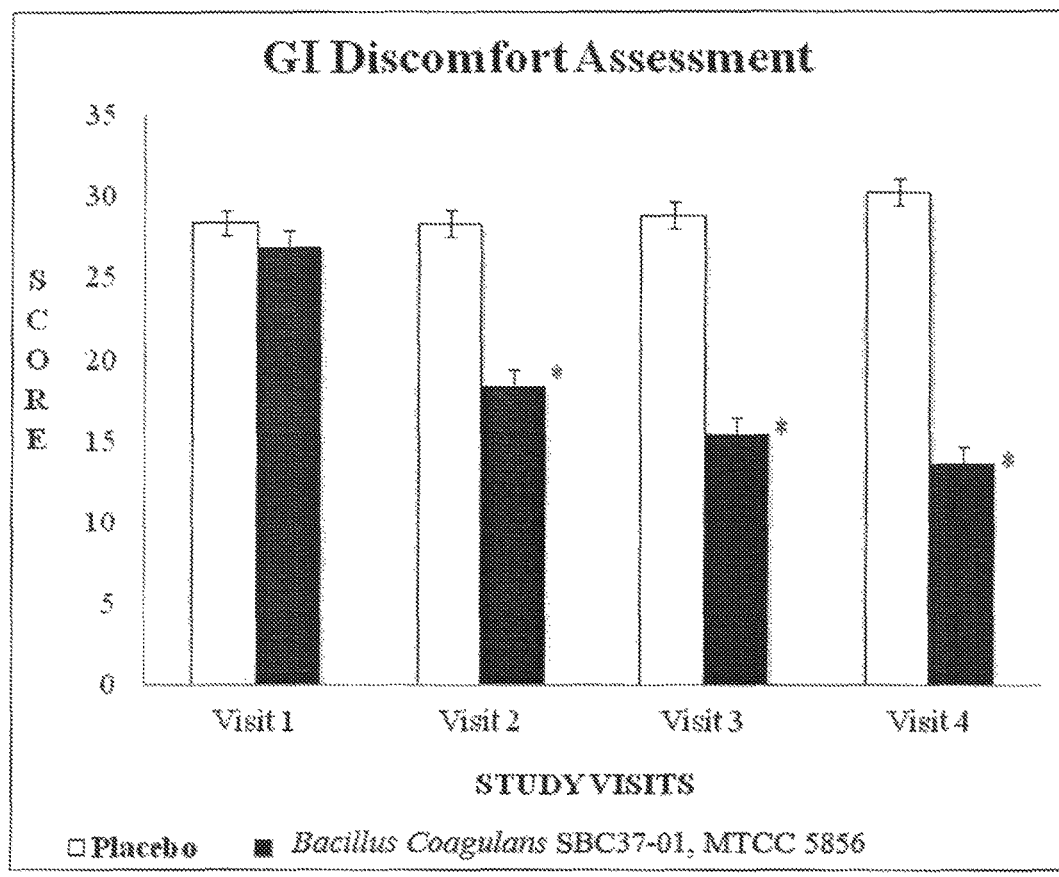
FIG. 3 shows the graphical representation for the gastrointestinal discomfort assessment.
Figure 4:
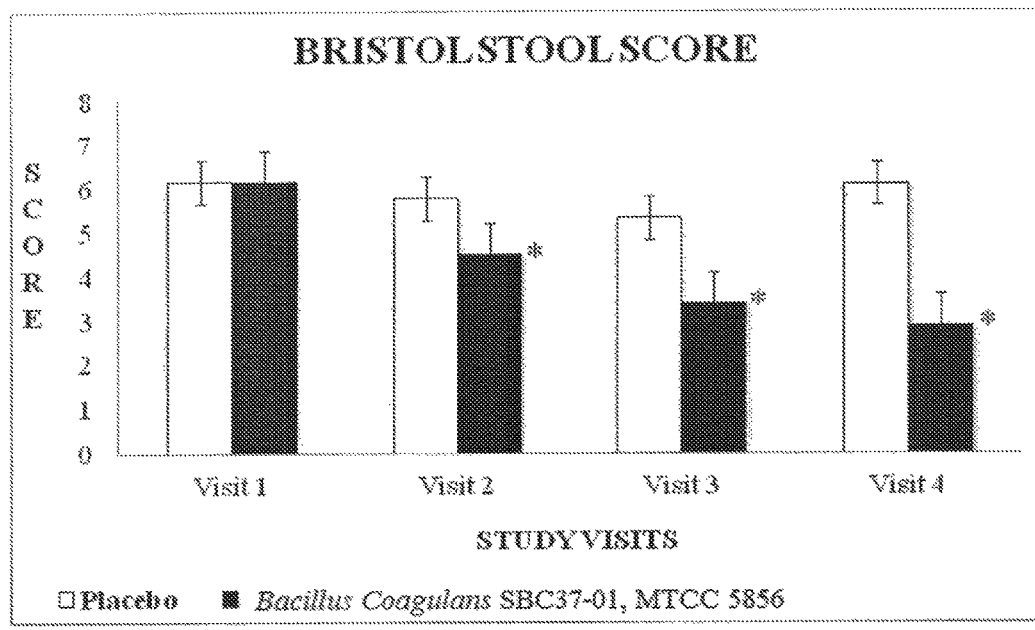
FIG. 4 shows the graphical representation for the Bristol stool score.
Figure 5:
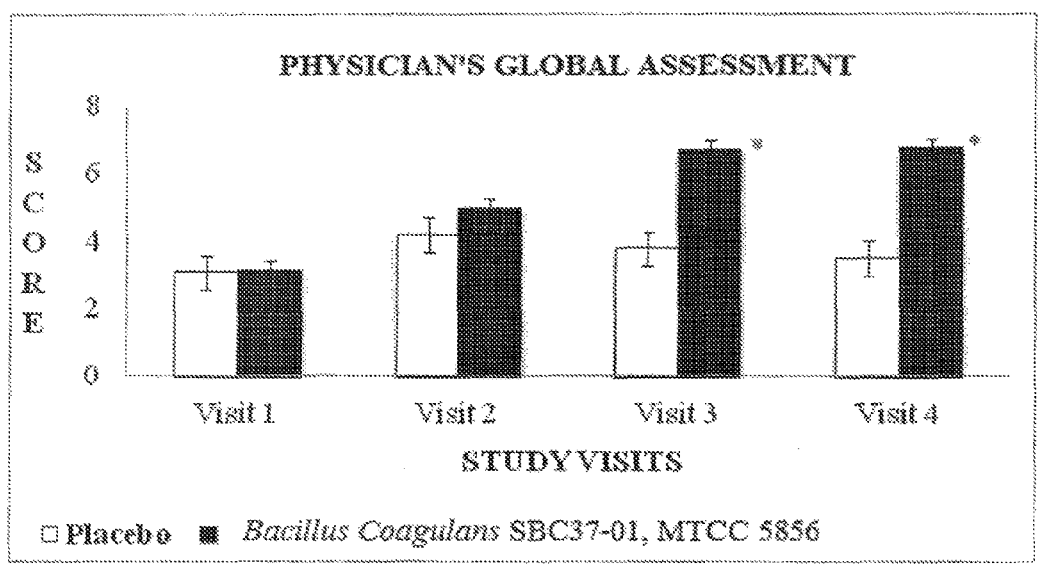
FIG. 5 shows the graphical representation for the Physician's Global Assessment.
Figure 6:
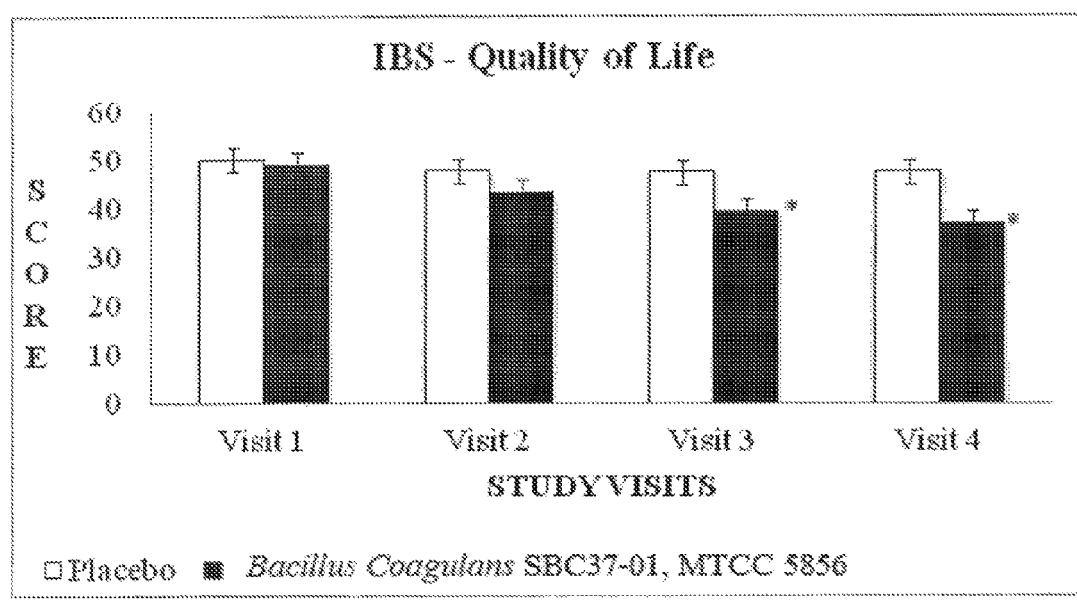
FIG. 6 shows the graphical representation for Irritable Bowel Syndrome-Quality of Life Assessment

(B) EFFICACY: Efficacy assessments like VAS score (FIG. 2), Gastrointestinal Discomfort Assessment Score (FIG. 3), Bristol Stool Score (FIG. 4), Physician's Global Assessment Score (FIG. 5), IBS Quality of Life Assessment Score (FIG. 6) were found to be statistically significant (p<0.01) when compared between baseline and visit 4 of the *Bacillus coagulans* SBC37-01, MTCC 5856 group patients, while there was no statistical significance between the baseline and visit 4 values for placebo group patients. The change in the efficacy assessments was significant (p<0.01) between the two treatment groups when their respective visit 4 values were analyzed.

(C) Other efficacy Measures: As bloating, vomiting, diarrhea, abdominal pain & stool frequency are common clinical symptoms of IBS, change in these trends (which were part of GI discomfort questionnaire), throughout the study period was analyzed as other efficacy measures. The 'p' value suggests that there is a statistically significant change in these symptoms from baseline to final visits, between the active and placebo receiving group of patients. This implies that patients who received *Bacillus coagulans* SBC37-01, MTCC 5856 had a significant change/decrease in clinical symptoms like bloating, vomiting, diarrhea, abdominal pain towards end of the study including the stool frequency (Table 5).

Discussion:

Out of 36 randomized patients, 31 completed the study. The first patient was enrolled on 4 Mar. 2014 and the last patient completed the study on 28 Jul. 2014. One subject discontinued the study after the second study visit, while the remaining 4 subjects dropped out of study after third study visit. The ratio of male to female subjects completed all study visits is 14:17, 3 males and 2 females dropped out of study. All of them cited personal reasons for opting out of study. While an analysis at the end of the study revealed that 4 out of 5 dropped out subjects were receiving placebo. By considering Last Observation Carry Forward, 35 subjects [17 Placebo+18 *Bacillus coagulans* SBC37-01, MTCC 5856] data were considered for efficacy analysis. Whereas for safety analysis, 31 [14 Placebo +17 *Bacillus coagulans* SBC37-01, MTCC 5856] subjects' data were considered. None of the enrolled subjects had abnormal medical history, except for Gastro-intestinal. Around 10 subjects (27.78%) had earlier GI related medical history which had no interference with IBS. No abnormality in physical findings was observed on the screening visit or during the study visits. Vital signs like blood pressure, pulse rate, respiratory rate and heart rate were normal on the screening visits and during the study visits. No statistically significant changes in vitals observed between baseline and visit 4 or between the treatment groups (Table 6).

(A) VAS: A general scale of 0 to 10 ranging from no pain to excruciating/worst possible pain was used to indicate the severity of the pain by the IBS patients through the study periods. Comparative analysis of Visual Analog Scale score indicates that the mean score of approximately 6.5 at baseline visit for both the treatment groups showed a steady decrease and ended up at a value of 2.94 for active treatment group of patients (*Bacillus coagulans* SBC37-01, MTCC 5856), whereas the placebo receiving group patients showed no signs of improvement in the pain with a mean values of 6.44 in the final visit.

(B) Gastrointestinal discomfort assessment score: A validated GI discomfort questionnaire was used for the assessment of none (0) to unbearable (150) dis-comfortness of GI, to all the study subjects. All the subjects were on mild to moderate IBS patients, the mean GI discomfort score was around 28.39 and 26.94 between the placebo and active treatment groups respectively on the baseline visit. Towards end of the study, the active treatment group patients gave a mean score of 13.56 which is a statistically significant not only from their baseline visit values but also from the mean values of placebo receiving group patients (30.29), on the final visit.

(C) Bristol Stool Score: As per this type 1 stools indicate—separate hard lumps, like nuts in terms of stool consistency, type 2: Sausage shaped but lumpy, type 3: Like a sausage or snake but with cracks on its surface, type 4: Like a sausage or snake, smooth and soft, type 5: Soft blobs with clear cut edges, type 6: Fluffy pieces with ragged edges, a mushy stool, type 7: Watery, no solid pieces. Majority of the study patients reported to respective study sites with a mean Bristol stool score of 6.17 (mushy stool) at baseline visit. The stool consistency increased significantly for patients receiving active treatment with no significant change observed in placebo receiving group patients by end of the study. This score was administered by the investigator/designee to the study subjects.

(D) Physician's Global Assessment Score: This assessment indicates, chow much better does the patient feel' with score 0 indicating very poor while 10 indicates excellent. On the baseline visit, a mean score of 3.06 and 3.11 was reported by placebo and active treatment group patients respectively. On day 90 (visit 4), the score increased significantly (p<0.01) for the active treatment group patients with no statistically significant change in the placebo receiving patients. So, it can be concluded that as per Physicians' at three clinical sites, patients felt much better with *Bacillus coagulans* SBC37-01, MTCC 5856 (active) when compared to placebo.

(E) IBS Quality of Life Questionnaire: This is a self-report quality of life, measures specific to IBS that can be used to assess the impact of IBS and its treatment. It had 34 items with a 5 point response scale. Highest score indicates poor quality of life while low score indicates better QOL by the patients. Mean values of 49.4 and 48.78 on baseline visits were changed to 47.24 and 36.67 on final visit between placebo and active treatment receiving group patients respectively. It was observed that the quality of life was better in active treatment group patients. As this product is intended for targeting GI, special emphasis was given on few clinical symptoms and found no study product's (*Bacillus coagulans* SBC37-01, MTCC 5856) related adverse events like vomiting, diarrhea and abdominal pain reported throughout the study period.

(F) Other additional assessments performed were quantification of pathogenic bacteria from subjects' stool samples at various visits. At screening visit, thirteen patients' stools were reported to have pathogenic bacteria like *Citrobacter, Enterobacter, E. coli* (overall 36.11%), and the number remained same towards end of the study in both the treatment groups. No changes were observed between the placebo and treatment groups with reference to *E. coli* when analyzed at various study related visits (FIG. 7).

Conclusions:

IBS patients who received *Bacillus coagulans* SBC37-01, MTCC 5856 reported a significant change/decrease in their clinical symptoms like bloating, vomiting, diarrhea, abdominal pain and stool frequency towards end of the study. Along with standard treatment of care, Sompraz D (containing Domperidone 30 mg and 40 mg of Esomeprazole) & Metrogyl 400 (Metronidazole 400 mg) once a day, received by all the diarrhea predominant IBS study subjects (both placebo and active groups), *Bacillus coagulans* SBC37-01, MTCC 5856 receiving patients demonstrated significant efficacy ($p<0.01$) towards treatment of IBS when compared to placebo receiving group patients. There was only one Adverse Event (AE) reported across three clinical sites from 36 enrolled subjects. The lone AE was found to be 'not related/unrelated' to the study product. With no abnormal laboratory values, changes in the vital signs from baseline through visit 4, and with no statistical difference (p 0.05) between both the treatment groups, *Bacillus coagulans* SBC37-01, MTCC 5856 as dietary supplement could be confirmed as safe for human consumption. It even demonstrated good efficacy for IBS patients, in mitigating their clinical symptoms.

TABLE 1

Subject Demographics

| | Total |
|---|---|
| Age (years) | |
| N | 36 |
| Mean ± SD | 35.8 ± 10.91 |
| Median | 35.5 |
| Height (cm) | |
| N | 36 |
| Mean ± SD | 163.8 ± 7.67 |
| Median | 163.0 |
| Weight (kg) | |
| N | 36 |
| Mean ± SD | 65.3 ± 10.11 |
| Median | 63.0 |
| Body Mass Index (kg/m$^2$) | |
| N | 36 |
| Mean ± SD | 24.4 ± 3.06 |
| Median | 24.1 |
| Gender [n (%)] | |
| Male | 17 (47.22) |
| Female | 19 (52.78) |
| Tobacco History [n (%)] | |
| Non User | 34 (94.44) |
| Past User | 2 (5.56) |
| Drinking History [n (%)] | |
| Non Drinker | 35 (97.22) |
| Past Drinker | 1 (2.78) |

TABLE 2

Change in Body Weight & BMI from baseline to visit 4

| Parameter | Product | Baseline | Visit 4 | Change | p-value* |
|---|---|---|---|---|---|
| Weight (kg) | Placebo | 68.2 | 71.3 | 0.43 | 0.4346 |
| | *Bacillus coagulans* SBC37-01, MTCC 5856 | 62.3 | 62.6 | 1.06 | 0.1319 |
| Body Mass Index (kg/m$^2$) | Placebo | 24.9 | 25.1 | −0.13 | 0.5385 |
| | *Bacillus coagulans* SBC37-01, MTCC 5856 | 24.0 | 23.9 | 0.03 | 0.8648 |

*p-value is estimated from Paired t-test

TABLE 3

Schedule of Events

| Procedures | Screening | Visit 1 (Day 0) | Visit 2 (Day 30) | Visit 3 (Day 60) | Visit 4 (Day 90) | Follow Up (Atleast 15 days from last visit) |
|---|---|---|---|---|---|---|
| Informed consent | X | | | | | |
| Medical History | X | | | | | |
| Physical Examination | X | X | X | X | X | |
| Demographics [a] | | X | X | X | X | |
| Vital Signs [b] | X | X | X | X | X | |
| Hematology | X | | | | X | |
| Serum Chemistry | X | | | | X | |
| Stool Test | X | | | | X | X |
| Urine Pregnancy Test [c] | X | | | | | |
| Randomization | | X | | | | |
| IP Dispensing and Dosing | | X | X | X | | |
| VAS Assessment | | X | X | X | X | |
| Gastrointestinal Discomfort Questionnaire | | X | X | X | X | |
| Bristol Stool Score | | X | X | X | X | |
| Physician's Global Assessment | | X | X | X | | |
| Irritable Bowel Syndrome Quality of Life Questionnaire | | X | X | X | X | |
| Adverse Events | | X | X | X | X | X |
| Concomitant medications | X | X | X | X | X | X |

[a] Age, height, weight and BMI. Age at screening only
[b] Vital signs on Screening, Day 0, Day 30, Day 60 and Day 90.
[c] Urine pregnancy test at screening and on early termination, if any.

TABLE 4

Test for Amoebiasis

| | | Treatment | | |
|---|---|---|---|---|
| Visit | Test for Amoebiasis | XAXA01 n (%) | XAXA02 n (%) | Overall n (%) |
| Visit 0 (Screening) | Negative | 18 (100.0) | 18 (100.0) | 36 (100.0) |
| Visit 4 | Negative | 14 (100.0) | 17 (100.0) | 31 (100.0) |
| Visit 5 (Follow Up) | Negative | 14 (100.0) | 17 (100.0) | 31 (100.0) |

TABLE 5

Other efficacy measures from GI Discomfort Questionnaire

| Parameter | Visit | p-value Active vs. Placebo |
|---|---|---|
| Bloating | Visit1 | 0.8400 |
| | Visit2 | 0.6544 |
| | Visit3 | 0.3196 |
| | Visit4 | 0.0135* |
| Vomiting | Visit1 | 0.7193 |
| | Visit2 | 0.2650 |
| | Visit3 | 0.0718 |
| | Visit4 | 0.0129* |
| Diarrhoea | Visit1 | 0.8071 |
| | Visit2 | 0.7136 |
| | Visit3 | 0.3321 |
| | Visit4 | 0.0514* |
| Abdominal Pain | Visit1 | 0.6549 |
| | Visit2 | 0.7384 |
| | Visit3 | 0.3914 |
| | Visit4 | 0.0153* |
| Stool Frequency | Visit1 | 0.7136 |
| | Visit2 | 0.0511* |
| | Visit3 | 0.0014* |
| | Visit4 | 0.0012* |

*P-values significant between active and placebo only on visit 4 for all parameters except stool frequency where significant difference was observed from visit 2 onwards.

TABLE 6

Change in Vital Signs from baseline to visit 4

| Vital Parameter | Product | Baseline | Visit 4 | Change | p-value* |
|---|---|---|---|---|---|
| Systolic Blood Pressure (mmHg) | Placebo | 125.1 | 120.0 | −5.1 | 0.0072* |
| | Bacillus coagulans SBC37-01, MTCC 5856 | 124.2 | 120.9 | −3.3 | 0.1923 |
| Diastolic Blood Pressure (mmHg) | Placebo | 79.1 | 79.3 | −0.2 | 0.5117 |
| | Bacillus coagulans SBC37-01, MTCC 5856 | 78.0 | 77.1 | −0.9 | 0.3170 |

TABLE 6-continued

Change in Vital Signs from baseline to visit 4

| Vital Parameter | Product | Baseline | Visit 4 | Change | p-value* |
|---|---|---|---|---|---|
| Pulse Rate (Beats per minute) | Placebo | 78.1 | 79.8 | 1.7 | 0.5682 |
| | Bacillus coagulans SBC37-01, MTCC 5856 | 76.8 | 76.4 | −0.4 | 0.6875 |
| Heart Rate (Beats per minute) | Placebo | 72.8 | 77.4 | 4.9 | 0.2817 |
| | Bacillus coagulans SBC37-01, MTCC 5856 | 73.6 | 71.0 | −2.6 | 0.4834 |
| Respiratory Rate (Breaths per minute) | Placebo | 16.9 | 17.1 | 0.2 | 0.2123 |
| | Bacillus coagulans SBC37-01, MTCC 5856 | 16.7 | 16.8 | 0.1 | 0.4220 |

*P-value is estimated from Paired t-test

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A process for the therapeutic management of symptoms associated with diarrhea predominant irritable bowel syndrome in a human subject newly diagnosed with mild to moderate irritable bowel syndrome or previously untreated human subject with mild to moderate irritable bowel syndrome, said process comprising orally administering to said human subject *Bacillus Coagulans* SBC37-01, deposited under the accession number MTCC 5856 formulation, as a dietary supplement, the formulation containing not less than 2 billion spores at least 30 minutes before a meal, in the morning for a period of 90 days along with standard treatment of care once a day in a manner that a time gap of 4 hours is maintained between the administration of said dietary supplement and the standard treatment of care, wherein said administering enhances the assessed therapeutic efficacy of the standard treatment of care by ameliorating symptoms associated with the irritable bowel syndrome (IBS) in said subject.

2. The process according to claim 1 wherein said standard treatment of care comprising orally administering a combination of 30 mg of Domperidone and 40 mg of Esomeprazole together with 400 mg of Metronidazole once a day.

3. The process according to claim 1 wherein the symptoms associated with irritable bowel syndrome (IBS) are abdominal pain, bloating or visible distension of abdomen, constipation and loose stools.

* * * * *